United States Patent [19]
Gilis et al.

[11] Patent Number: 5,633,015
[45] Date of Patent: May 27, 1997

[54] BEADS HAVING A CORE COATED WITH AN ANTIFUNGAL AND A POLYMER

[76] Inventors: Paul M. V. Gilis, Schransdriesstraat 14, B-2340-Beerse; Valentin F. V. De Condé, Kolonie 57, B-3920-Lommel; Roger P. G. Vandecruys, Langstraat 108, B-2260-Westerlo, all of Belgium

[21] Appl. No.: 432,188
[22] PCT Filed: Aug. 27, 1993
[86] PCT No.: PCT/EP93/02327
  § 371 Date: Mar. 13, 1995
  § 102(e) Date: Mar. 13, 1995
[87] PCT Pub. No.: WO94/05263
  PCT Pub. Date: Mar. 17, 1994

[30] Foreign Application Priority Data
  Sep. 3, 1992 [EP] European Pat. Off. ........... 92202664.6

[51] Int. Cl.⁶ .................. A61K 9/16; A61K 9/50
[52] U.S. Cl. .......... 424/490; 424/493; 424/494; 424/499; 424/488; 424/489; 424/456
[58] Field of Search .............. 514/777; 424/488, 424/1.1, 489, 493, 490, 491

[56] References Cited

U.S. PATENT DOCUMENTS

| | | | |
|---|---|---|---|
| 4,855,326 | 8/1989 | Fuisz et al. | 514/777 |
| 5,049,374 | 9/1991 | Dansereau et al. | 424/1.1 |
| 5,213,811 | 5/1993 | Frisbee et al. | 424/493 |

Primary Examiner—Thurman K. Page
Assistant Examiner—William E. Benston, Jr.
Attorney, Agent, or Firm—Charles J. Metz

[57] ABSTRACT

The present invention is concerned with beads comprising a 25–30 mesh core, a coating of a hydrophilic polymer and an antifungal agent, and a seal outer coating layer; pharmaceutical dosage forms comprising said beads and a method of preparing said beads. Preferred antifungal agents are lipophilic azole antifungals, such as itraconazole and saperconazole.

18 Claims, No Drawings

BEADS HAVING A CORE COATED WITH AN ANTIFUNGAL AND A POLYMER

CROSS-REFERENCE TO RELATED APPLICATIONS

This application is based upon PCT Application Serial No. PCT/EP 93/02327, filed Aug. 27, 1993, which claims priority from European patent application Serial No. 92.202.664.6, filed on Sep. 3, 1992.

The present invention is concerned with a novel composition of antifungal agents which have low solubility in aqueous media, a process for preparing said composition and pharmaceutical dosage forms for oral administration comprising said novel composition.

The development of efficaceous pharmaceutical compositions of azole antifungals such as for example, itraconazole and saperconazole, is hampered considerably by the fact that said antifungals are only very sparingly soluble in water. The solubility and bioavailability of said compounds can be increased by complexation with cyclodextrins or derivatives thereof as described in WO 85/02767 and U.S. Pat. No. 4,764,604. Yet, there still exists an important demand for formulations of antifungal agents with good bioavailability for oral administration.

Itraconazole or (±)-cis-4-[4-[4-[4-[[2-(2,4-dichlorophenyl)-2-(1H-1,2,4-triazol-1-ylmethyl)-1,3-dioxolan-4-yl]methoxy]phenyl]-1-piperazinyl]phenyl]-2,4-dihydro-2-(1-methylpropyl)-3H-1,2,4-triazol-3-one, is a broadspectrum antifungal compound developed for oral, parenteral and topical use and is disclosed in U.S. Pat. No. 4,267,179. Its difluoro analog, saperconazole or (±)-cis-4-[4-[4-[[2-(2,4-difluorophenyl)-2-(1H-1,2,4-triazol-1-ylmethyl)-1,3-dioxolan-4-yl]methoxy]phenyl]-1-piperazinyl]-phenyl]-2,4-dihydro-2-(1-methoxypropyl)-3H-1,2,4-triazol-3-one, has improved activity against Aspergillus spp. and is disclosed in U.S. Pat. No. 4,916,134.

Unexpectedly, it has now been found that the incorporation of poorly soluble antifungal agents in hydrophilic polymers and applying this mixture as a coat film over many small beads, yields a composition with good bioavailability which can conveniently be manufactured and which is suitable for preparing pharmaceutical dosage forms for oral administration.

In particular the present invention is concerned with beads which comprise (a) a central, rounded or spherical core, (b) a coating film of a hydrophilic polymer and an antifungal agent and (c) a seal-coating polymer layer, characterized in that the core has a diameter of about 600 to about 700 µm (25–30 mesh).

Beads obtainable from 25–30 mesh cores comprise approximately, by weight based on the total weight of the bead: (a) 20 to 60 percent core material; (b) 25 to 50 percent hydrophilic polymer; (c) 10 to 25 percent antifungal agent; and (d) 2 to 5 percent seal coating polymer.

The particular size of the cores is of considerable importance. On the one hand, if the cogs are too large, there is less surface area available for applying the drug coating layer, which results in thicker coating layers. This raises problems in the manufacturing process as an intensive drying step is needed to reduce residual solvent levels in the coating layer. The intense drying conditions may adversely effect drug dissolution from the beads and should therefore be controlled extremely well during the manufacturing process. On the other hand, small cores have a larger total surface available for coating resulting in thinner coating layers. Consequently a far less intensive drying step can be used to decrease residual solvents levels. Cogs which are too small, e.g. 30–35 mesh cores, however, have the disadvantage of showing considerable tendency to agglomerate during the coating process. Therefore, 25–30 mesh cons represent the optimum size where neither agglomeration nor an intensive drying step unduly constraint the manufacturing process.

Materials suitable for use as cores in the beads according to the present invention are manifold, provided that said materials are pharmaceutically acceptable and have appropriate dimensions (about 25–30 mesh) and firmness. Examples of such materials are polymers e.g. plastic resins; inorganic substances, e.g. silica, glass, hydroxyapatite, salts (sodium or potassium chloride, calcium or magnesium carbonate) and the like; organic substances, e.g. activated carbon, acids (citric, fumaric, tartaric, ascorbic and the like acids), and saccharides and derivatives thereof. Particularly suitable materials are saccharides such as sugars, oligosaccharides, polysaccharides and their derivatives, for example, glucose, rhamnose, galactose, lactose, sucrose, mannitol, sorbitol, dextrin, maltodextrin, cellulose, sodium carboxymethyl cellulose, starches (maize, rice, potato, wheat, tapioca) and the like saccharides.

A particularly preferred material suitable for use as cons in the beads according to the present invention is represented by 25–30 mesh sugar spheres (NF XVII, p 1989) which consist of 67.5%–91.5% (w/w) sucrose, the remainder being starch and possibly also dextrines, and which are pharmaceutically inert or neutral.

The drug coating layer preferably comprises a hydrophilic polymer such as hydroxypropyl methylcellulose (Methocel®, Pharmacoat®), methacrylate (Eudragit E®), hydroxypropylcellulose (Klucel®), or a polyvidone. Preferably hydroxypropyl methylcellulose with low viscosity, i.e. about 5 mPa.s, is used, e.g. hydroxypropyl methylcellulose 2910 5 mPa.s. Preferred antifungal agents for use as drugs in said drug coating layer are lipophilic azole antifungals, in particular intaconazole and saperconazole. Optimum dissolution results are obtained when using a drug: polymer ratio (w/w) of about 1:1 to about 1:2, preferably about 1:1.5. In the drug coating layer, the drug substance is present in a solid dispersion or solution state as can be confirmed by differential scanning calorimetry.

A seal coating polymer layer is applied to the drug coated cores to prevent sticking of the beads which would have the undesirable effect of a concomitant decrease of the dissolution rate and of the bioavailability. Preferably a thin layer of polyethylene glycol (PEG), in particular polyethylene glycol 20000 is used as a seal coating polymer layer.

The preferred beads comprise approximately: (a) 26 to 38 percent sugar; (b) 32 to 33 percent hydroxypropyl methylcellulose 2910 5 mPa.s; (c) 21 to 22 percent itraconazole or saperconazole; and (d) 3 to 4 percent polyethylene glycol 20000.

In addition, the beads according to the present invention may further contain various additives such as thickening agents, lubricants, surfactants, preservatives, complexing and chelating agents, electrolytes or other active ingredients, e.g. antiinflammatory agents, antibacterials, disinfectants or vitamins.

The beads according to the present invention can conveniently be formulated into various pharmaceutical dosage forms. Suitable dosage forms comprise an effective antifungal amount of beads as described hereinbefore. Preferably, the beads are filled in hard-gelatin capsules such that an amount of, for example, 50 or 100 mg of the active ingredient is available per dosage form. For example, hard-gelatin capsules of size 0 are suitable for formulating beads comprising 20 to 25 percent by weight itraconazole or saperconazole, equivalent to about 100 mg active ingredient.

The beads according to the present invention are conveniently prepared in the following manner. A drug coating solution is prepared by dissolving into a suitable solvent system appropriate amounts of an antifungal agent and a hydrophilic polymer. A suitable solvent system comprises a mixture of methylenechloride and an alcohol, preferably ethanol which may be denatured, for example, with butanone. Said mixture should comprise at least 50% by weight of methylenechloride acting as a solvent for the drug substance. As hydroxypropyl methylcellulose does not dissolve completely in methylenechloride, at least 10% alcohol has to be added. Preferably a relatively low ratio of methylenechloride/alcohol is used in the coating solution, e.g. a ratio methylenechloride/ethanol ranging from 75/25 (w/w) to 55/45 (w/w), in particular about 60/40 (w/w). The amounts of solids, i.e. antifungal agent and hydrophilic polymer, in the drug coating solution may range from 7 to 10% (w/w) and preferably is about 8%.

The drug coating process of the 25–30 mesh cores is conveniently conducted in a fluidized bed granulator (e.g. Glatt type WSG-30) equipped with a Wurster bottom spray insert (e.g. an 18 inch Wurster insert). Obviously the process parameters will depend on the equipment used.

The spraying rate should be regulated carefully. Too low a spraying rate can cause some spray drying of the drug coating solution and result in a loss of product. Too high a spraying rate will cause overwetting with subsequent agglomeration. Agglomeration being the most serious problem, lower spraying rates may be used initially, to be increased as the coating process proceeds and the beads grow larger.

The atomizing air pressure with which the drug coating solution is applied also influences the coating performance. Low atomizing air pressure results in the formation of larger droplets and an increased tendency toward agglomeration. High atomizing air pressure could conceivably carry the risk of spray drying of the drug solution, but this was found not to be a problem. Consequently, atomizing air pressure may be set at nearly maximum levels.

Fluidizing air volume can be monitored by operating the exhaust air-valve of the apparatus and should be set in such a manner that optimum bead circulation is obtained. Too low an air volume will cause insufficient fluidization of the beads; too high an air volume will interfere with the bead circulation due to countercurrent air streams developing in the apparatus. In the present process optimum conditions were obtained by opening the exhaust air valve to about 50% of its maximum and gradually increasing the opening thereof to about 60% of the maximum as the coating process proceeded.

The coating process is advantageously conducted by employing an inlet-air temperature ranging from about 50° C. to about 55° C. Higher temperatures may speed up the process but have the disadvantage that solvent evaporation is so rapid that the coating liquid is not spread uniformly on the surface of the beads resulting in the formation of a drug coating layer with high porosity. As the bulk volume of the coated beads increases, drug dissolution may decrease significantly to unacceptable levels. Obviously, the optimum process temperature will further depend on the equipment used, the nature of the core and the antifungal agent, the batch volume, the solvent and the spraying rate.

Parameter settings for optimum coating results are described in more detail in the example hereinafter. Running the coating process under those conditions was found to yield very reproducible results.

In order to decrease residual solvent levels in the drug coating layer, the drug coated cores can conveniently be dried in any suitable drying apparatus. Good results may be obtained using a vacuum tumbler-drier operated at a temperature from about 60° C. to about 90° C., preferably about 80° C., a reduced pressure ranging from about 150–400 mbar (15–40 kPa), preferably 200–300 mbar (20–30 kPa), for at least 24 hours, preferably about 36 hours. The vacuum tumbler-drier is conveniently rotated at its minimum speed, e.g. 2 to 3 rpm. After drying, the drug coated cores may be sieved.

The seal coating polymer layer is applied to the drug coated cores in the fluidized bed granulator with Wurster bottom spray insert. The seal coating solution can be prepared by dissolving an appropriate amount of a seal coating polymer into a suitable solvent system. Such a system, is, e.g. a mixture of methylene chloride and an alcohol, preferably ethanol which may be denatured with, for example, butanone. The ratio of methylene chloride/alcohol used may be similar to the ratio used in the drug coating process and thus can range from about 75/25 (w/w) to about 55/45 (w/w) and in particular is about 60/40 (w/w). The amount of seal coating polymer in the seal coating spraying solution may range from 7 to 12% (w/w) and preferably is about 10%. The seal coating spraying solution is advantageously stirred during the seal coating process. The parameter setting for conducting this last step is essentially similar to that used in the drug coating process. Appropriate conditions are described in more detail in the example hereinafter.

A further drying step may be required after applying the seal coating polymer layer. Excess solvents could easily be removed while operating the apparatus at the parameter settings used for about 5 to 15 minutes after the spraying had been completed.

Both the drug coating process and the seal coating process are preferably conducted under an inert atmosphere of e.g. nitrogen. The coating equipment should preferably be grounded and provided with an appropriate solvent recovery system containing an efficient condensing system.

The drug coated and seal coated beads may be filled in hard-gelatin capsules using standard automatic capsule filling machines. Suitable earthing and de-ionisation equipment can advantageously prevent development of electrostatic charges.

Capsule filling speed may influence weight distribution and should be monitored. Good results are obtained when operating the equipment at about 75% to 85% of the maximum speed and in many cases when operating at full speed.

Using the process parameters described above, a convenient, reproducible manufacturing method for preparing beads comprising a 25–30 mesh core, a drug coat layer of an antifungal agent and a hydrophilic polymer and a thin seal-coating polymer layer can be obtained. Pharmacokinetic studies showed that the thus obtained beads have excellent dissolution and bioavailability properties.

EXAMPLE a) Itraconazole Spraying Solution

An inox vessel was charged with methylene chloride (375 kg) and denatured ethanol (250 kg) through a filter (5μ).

Itraconazole (21.74 kg) and hydroxypropyl methylcellulose 2910 5 mPa.s (32.61 kg) was added while stirring. Stirring was continued until complete dissolution was obtained (A suitable saperconazole spraying solution was obtained using an identical procedure).

b) Seal-Coating Spraying Solution

An inox vessel was charged with methylene chloride (21.13 kg) and polyethylene glycol 20000 (Macrogol 20000) (3.913 kg) while stirring. Denatured ethanol (14.09 kg) was added and the solution was stirred until homogeneous.

c) Drug Coating Process

A fluidized-bed granulator (Glatt, type WSG 30) equipped with a 18 inch Wurster (bottom spray) insert was loaded with 25–30 mesh (600–700 μm) sugar spheres (41.74 kg). The spheres were warmed with dry air of 50°–55° C. The fluidizing air volume was controlled by opening the exhaust air valve to approximately 50% of its maximum in the beginning, increasing up to 60% at the end of the spraying process. The previously prepared itraconazole spraying solution was then sprayed on the spheres moving in the apparatus. The solution was sprayed at an initial delivery rate of about 600 to 700 g.min$^{-1}$ at an atomizing air pressure of about 3.5 kg/cm$^2$ (0.343 MPa). After delivery of about 30% of the spraying solution, the delivery rate was increased to 700–800 g/min.

When the spraying process was completed, the coated spheres were dried by further supplying dry air of 50°–55° C. for about 10 minutes. The coated spheres were then allowed to cool in the apparatus by supplying dry air of 20°–25° C. for about 10 to 20 minutes. The apparatus was emptied and the coated spheres were collected.

d) In-Between Drying

In order to minimize residual solvent levels the coated spheres were then subjected to a drying step. The coated spheres were introduced in a vacuum tumbler-drier and dried for at least 24 hours, preferably about 36 hours, at a temperature of about 80° C. at a pressure of about 200–300 mbar (20–30 kPa). The tumbler-drier was operated at its minimal rotation speed (2 to 3 rpm). The dried coated spheres were sieved with a sieve (Sweco S24C; sieve mesh width 1.14 mm).

e) Seal-Coating Process

The dried coated spheres were introduced again in the fluidized-bed granulator equipped with the Wurster insert and warmed with dry air of 50°–55° C. The previously prepared seal-coating spraying solution was then sprayed on the coated spheres moving in the apparatus. The solution was sprayed at an delivery rate of about 400 to 500 g.min$^{-1}$, at an atomizing air pressure of about 2.5 bar (0.25 MPa). When the spraying process was completed, the beads were dried by further supplying dry air of 50°–55° C. for 10 min. The coated spheres were then allowed to cool in the apparatus by supplying dry air of 20°–25° C. for about 5 to 15 minutes. The beads were removed from the apparatus and stored in suitable containers.

f) Capsule Filling

The drug coated beads were filled into hard-gelatin capsules (size 0) using standard automatic capsule filling machines (e.g. Model GFK-1500, Höffliger and Karg. Germany). In order to obtain capsules with good weight distribution, capsule filling speed was reduced to about 75–85% of the maximum speed. Each capsule received approximately 460 mg beads, equivalent to about 100 mg itraconazole. Using the process parameters described above, itraconazole 100 mg hard-gelatin capsules were obtained which met all the requirements, in particular the dissolution specifications. Saperconazole 100 mg hard-gelatin capsules could be obtained by conducting the above-described procedures and using the saperconazole spraying solution.

We claim:

1. A bead comprising:
   a) a central, rounded or spherical core;
   b) a coating film of a hydrophilic polymer and an antifungal agent selected from the group consisting of itraconazole and saperconazole, and
   c) a seal-coating polymer layer, characterized in that the core has a diameter of from about 600 to about 700 μm (25–30 mesh).

2. A bead according to claim 1 comprising by weight based on the total weight of the bead:
   a) 20 to 60 percent core material;
   b) 25 to 50 percent hydrophilic polymer;
   c) 10 to 25 percent antifungal agent; and
   d) 2 to 5 percent seal-coating polymer.

3. A bead according to claim 2 wherein the core material is a 25–30 mesh sugar sphere, the hydrophilic polymer is hydroxypropyl methylcellulose and the antifungal agent is itraconazole.

4. A bead according to claim 3 wherein the weight to weight ratio of antifungal agent: hydrophilic polymer is about 1:1 to about 1:2.

5. A bead according to claim 2 wherein the seal-coating polymer is polyethylene glycol.

6. A bead according to claim 2 comprising approximately:
   a) 26 to 38 percent sugar;
   b) 32 to 33 percent hydroxypropyl methylcellulose 2910 5 mPa.s.;
   c) 21 to 22 percent itraconazole; and
   d) 3 to 4 percent polyethylene glycol 20000.

7. A pharmaceutical dosage form comprising an effective antifungal amount of beads as defined in claim 1.

8. A pharmaceutical dosage form comprising an effective antifungal amount of beads as defined in claim 2.

9. A pharmaceutical dosage form comprising an effective antifungal amount of beads as defined in claim 3.

10. A pharmaceutical dosage form comprising an effective antifungal amount of beads as defined in claim 4.

11. A pharmaceutical dosage form comprising an effective antifungal amount of beads as defined in claim 5.

12. A pharmaceutical dosage form comprising an effective antifungal amount of beads as defined in claim 6.

13. A pharmaceutical dosage form wherein the dosage form is a hard-gelatin capsule comprising an effective antifungal amount of itraconazole or saperconazole in the form of beads as defined in claim 1.

14. A pharmaceutical dosage form wherein the dosage form is a hard-gelatin capsule comprising an effective antifungal amount of itraconazole or saperconazole in the form of beads as defined in claim 2.

15. A pharmaceutical dosage form wherein the dosage form is a hard-gelatin capsule comprising an effective antifungal amount of itraconazole in the form of beads as defined in claim 3.

16. A pharmaceutical dosage form wherein the dosage form is a hard-gelatin capsule comprising an effective antifungal amount of itraconazole in the form of beads as defined in claim 4.

17. A pharmaceutical dosage form wherein the dosage form is a hard-gelatin capsule comprising an effective antifungal amount of itraconazole in the form of beads as defined in claim 5.

18. A pharmaceutical dosage form wherein the dosage form is a hard-gelatin capsule comprising an effective antifungal amount of itraconazole in the form of beads as defined in claim 6.

* * * * *

UNITED STATES PATENT AND TRADEMARK OFFICE
CERTIFICATE OF CORRECTION

PATENT NO. : 5,633,015 Page 1 of 1
DATED : May 27, 1997
INVENTOR(S) : Paul M. V. Gilis, Valentin F. V. De Conde and Roger P. G. Vandercruys It is certified that error appears in the above-identified patent and that said Letters Patent is hereby corrected as shown below:

Column 1,
Line 59, replace "cogs" with -- cores --.

Column 2,
Line 3, replace "cogs" with -- cores --.
Line 6, replace "cons" with -- cores --.
Line 25, replace "cons" with -- cores --.
Line 39, replace "intaconazole" with -- itraconazole --.

Column 6,
Line 4, replace "H6offliger" with -- Hoffliger --.

Signed and Sealed this

Seventeenth Day of September, 2002

Attest:

JAMES E. ROGAN
Attesting Officer   Director of the United States Patent and Trademark Office